United States Patent [19]

Maurice et al.

[11] Patent Number: 4,863,574

[45] Date of Patent: Sep. 5, 1989

[54] METHOD OF MANUFACTURING A FILM OF POLYPARAPHENYLENE AND APPLICATIONS OF THE RESULTING POLYPARAPHENYLENE FILM

[75] Inventors: François Maurice, Perros-Guirec; Gérard Froyer; Yvan Pelous, both of Lannion; Michel Petit, Montmorency; Jean-Francois Fauvarque, Paris, all of France

[73] Assignee: Centre National de la Recherche Scientifique, Paris, France

[21] Appl. No.: 941,011

[22] Filed: Dec. 12, 1986

[30] Foreign Application Priority Data

Dec. 17, 1985 [FR] France .................................. 8518666

[51] Int. Cl.$^4$ .............................................. C25B 3/00
[52] U.S. Cl. ...................... 204/59 R; 204/72; 350/357; 252/500
[58] Field of Search .............. 204/59 R; 252/500; 429/213, 249; 350/357

[56] References Cited

U.S. PATENT DOCUMENTS 4,517,116 5/1985 Ivory et al. ........................ 252/518
4,559,112 12/1985 Tamamura et al. .............. 204/59 R
4,601,849 7/1986 Yata ..................................... 252/500

OTHER PUBLICATIONS

Yamamoto et al., Bull Chem. Soc., Japan 51 (1978), pp. 2091-2097.
Liogen'kii et al., Chem. Abst. 92 (1980), #7906h.
Chem. Abstracts 10th Collective 1981, p. 41124c.

Primary Examiner—John F. Niebling
Assistant Examiner—Steven P. Marquis
Attorney, Agent, or Firm—Fulbright & Jaworski

[57] ABSTRACT

The invention relates to a method of manufacturing a film of polyparaphenylene by electro-polymerization, the method being the type using electrochemical reduction of a monomer having the following formula:

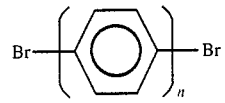

where n is an integer lying in the range 1 to 4, the method taking place in an electrochemical cell (1) including a reference electrode (4), a working electrode (2), and a counter electrode (3), said electrodes being immersed in an electrolyte including one or more aprotic solvents, at least one of which is bipolar, and an anhydrous background salt in the presence of an organometallic catalyst of the $NiX_2L$ type where X is a halogen and L is a binder, the working electrode being a solid cathode and the catalyst/monomer ratio lying in the range 0.1 to 1.

11 Claims, 2 Drawing Sheets

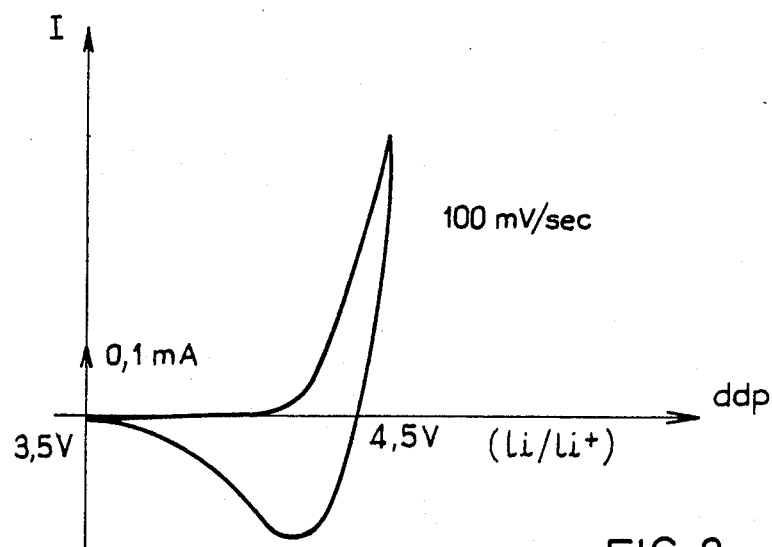
FIG_2
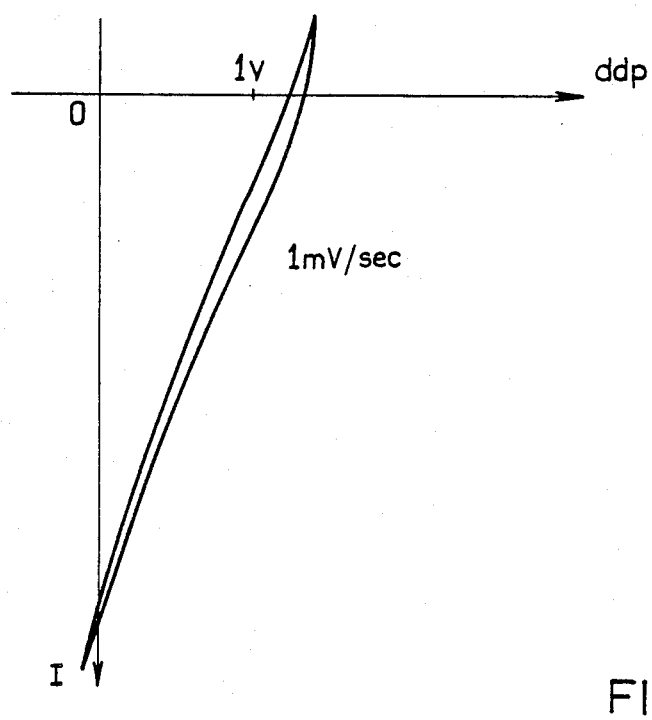
FIG_3

METHOD OF MANUFACTURING A FILM OF POLYPARAPHENYLENE AND APPLICATIONS OF THE RESULTING POLYPARAPHENYLENE FILM

The present invention relates to a method of manufacturing a film of polyparaphenylene by electrochemical reduction, and it also relates to applications of the resulting polyparaphenylene film to making photovoltaic cells, oxygen detectors/meters, electrochromic cells, and batteries.

Polyparaphenylene is referred to below as PPP.

BACKGROUND OF THE INVENTION

PPP is a semiconductive polymer having low conductivity. Its general formula is $(C_6H_4)_x$, where x is the degree of polymerization. PPP becomes electrically conductive only when doped by electron acceptors (P type doping) or by electron donors (N type doping).

In the above-mentioned applications, doped or undoped PPP is advantageously used in the form of a very thin film. In particular:

the photovoltaic application requires thicknesses of less than $10^{-7}$ m in order to minimize resistance; and the electrochromic application requires thicknesses of less than 1 micron in order to retain an adequate switching speed.

No prior art method of preparing PPP is capable of providing it in the form of a thin film having uniform and well-determined characteristics.

Thus, for example, the methods of synthesis described by Kovacic et al (P. Kovacic, A. Kyriakis, J.Am. Chem. Soc. 85, 454 (1963)), or by Fauvarque et al (J. F. Fauvarque, M. A. Petit, F. Pfluger, A. Jutand, C. Chevrot, M. Troupel, Makromol Chem. Rapid Commun. 4, 455 (1983)), lead to the formation of powders which are not suitable for providing films since they are insoluble and unmeltable. A pelleting press cannot be used to obtain thicknesses of less than 30 μm (because of mechanical strength problems). It is thus necessary and advantageous to synthesize PPP directly in the form of thin films.

Other writers have proposed obtaining films by electrosynthesis by oxidizing benzene under the following conditions:

oxidizing benzene or biphenyl in acetonitrile (T. Osa, A. Yildiz, T. Kurvana—J.A.C.S. 91 (14) (1969) 3994);

oxidizing benzene in $SO_2$ at $-20°$ C. (M. Delamar, P. C. Lacaze, J. Y. Dumousseau, J. E. Dubois—Electrochimica acta 27-1 (1982) 61);

oxidizing benzene at the benzene-HF interface (A. F. Shepard, B. F. Dannels—J polym. sci. A.1 4 (1966) 511, and I. Rubinstein—electrochem. soc. 130.7 (1983) 1506); and oxidizing benzene in nitrobenzene (K. Kaeriyanma, M. A. Sato, K. Someno, S. Tanaka—J. Chem. soc. chem. commun. (1984) 1199).

However, these four methods provide films which suffer from the following defects:

preparation is difficult (in HF or liquid $SO_2$), or takes place under limiting conditions of solvent use;

there is no guarantee that the phenylene units will be chained in the para positions only; and OH, oxygen or nitrogen are present in the film.

Other writers have proposed obtaining films by electrosynthesis by reducing the following in acetonitrile:

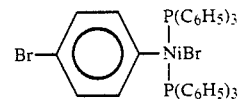

(G. Schiavon, G. Zotti, G. Bontempelli—J. electro. anal. chem. 161 (1984) 323).

This method gives a film in which the phenyl units are chained in the para positions, but in which a nickel atom is incorporated once every 7 or 8 cycles.

SUMMARY OF THE INVENTION

The present invention provides a method of manufacturing a polyparaphenylene film by electro-polymerization, the method being of the type including electrochemical reduction of a monomer having the formula:

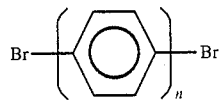

where n is an integer lying in the range 1 to 4, said electrochemical reduction taking place in an electrochemical cell comprising a reference electrode, a working electrode, and a counter electrode, all immersed in an electrolyte including one or more aprotic solvents, with at least one of said solvents being bipolar, and an anhydrous background salt in the presence of an organometallic catalyst of the $NiX_2L$ type where X is a halogen and L is a binder, the method including the improvement whereby the monomer is electrochemically reduced in a one-compartment cell, and whereby the working electrode is a solid cathode and the ratio of catalyst to monomer lies in the range 0.1 to 1 and is in particular about 0.25.

Thus, PPP is synthesized by making use of a particular method of a general type known in the prior art; this method consists in electrochemically reducing a monomer having the formula:

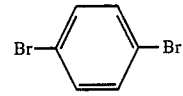

with the electrochemical reduction corresponding to the following reaction diagram (where n is the degree of polymerization):

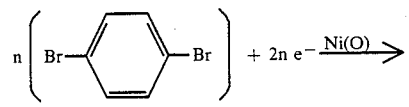

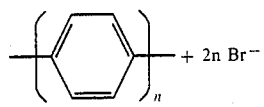

For the catalyst, recent results have shown that 0 valence nickel complexes can be generated in situ by electrochemically reducing $NiX_2L_2$, where X=Cl or Br, and L=P(C$_6$H$_5$)$_3$ or L$_2$ =(C$_6$H$_5$)$_2$—P—CH$_2$—CH$_2$—P—(C$_6$H$_5$)$_2$ As a consequence, these complexes are immediately made use of for synthesizing PPP by electrically reducing dibromobenzene.

In the prior art, the above-mentioned electropolymerization takes place under an argon atmosphere at ambient temperature in a three-electrode cell whose anode and cathode compartments are separated by a disk of sintered glass.

The electrodes are conventionally made of mercury for the cathode or working electrode, of lithium for the anode, and of silver for the reference electrode.

The main drawback of this method is that PPP is obtained in powder form and is therefore unusable for many applications. In numerous fields, and in particular for the applications of PPP mentioned in the examples below, it is necessary to have PPP in the form of a film which is highly uniform and very thin.

The Applicants have shown that such a working electrode or cathode constituted by the surface of liquid mercury is capable of synthesizing PPP in powder form only. They have also shown that using a solid working electrode instead of the prior art liquid electrode gives rise to PPP being synthesized as a film.

Thus, in accordance with the present invention, a preferably one-compartment cell is used which comprises:

a solid cathode made preferably from the group constituted by graphite, vitreous carbon, gold, nickel, platinum, glass covered with a conductive oxide of the SnO$_2$ or of the indium tin oxide (ITO) type, and metal-covered glass;

an anode or counter electrode which is preferably soluble, for example made of lithium or of magnesium or which is not soluble, for example made of gold or platinum; and a reference electrode which is preferably made of silver/silver perchlorate.

According to the present invention, these three electrodes are immersed in an electrolyte comprising one or more aprotic solvents. Preferably, the electrolyte is constituted by a mixture of two solvents comprising an aprotic solvent and a bipolar aprotic solvent in a volume ratio of ⅔ to ⅓, respectively. Thus, for example the electrolyte may be a mixture of ⅔ tetrahydrofuran (THF) and ⅓ hexamethylphosphorotriamide (HMPT).

Preferably, in accordance with the present invention, an anhydrous background salt is added to the electrolyte, said salt having a degree of ionic conductivity and not providing any protons.

The salt may be chosen from the group: LiClO$_4$, NaBF$_4$, NBu$_4$BF$_4$.

The monomer used in accordance with the present invention has the following formula:

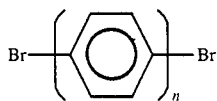

where n is an integer lying in the range 1 to 4. n is preferably equal to 1 or 2, with 4,4' dibromobiphenyl giving rise to particularly effective results.

The Applicants have also shown that the catalyst/monomer ratio should lie between about 0.1 and 1.

Preferably, in order to obtain uniform PPP films in accordance with the invention, this ratio should be close to 0.25.

In accordance with an additional feature of the present invention, the working electrode is subjected to a voltage lying in the range −2.2 and −2.8 volts relative to the Ag/Ag+ reference electrode, and preferably to a voltage of −2.5 volts.

Thus, in a preferred implementation of the method according to the invention, a thin film of PPP is synthesized on a sheet of glass covered in the ITO conductive oxide.

BRIEF DESCRIPTION OF THE DRAWINGS

An implementation of the invention is described by way of example with reference to the accompanying drawings, in which:

FIG. 2 is a voltage-current chart showing the effect of applying a cyclic voltage to doped PPP; and FIG. 3 is a voltage-current chart showing the photovoltaic nature of undoped PPP.

DETAILED DESCRIPTION OF PREFERRED EMBODIMENTS

Figure 1:
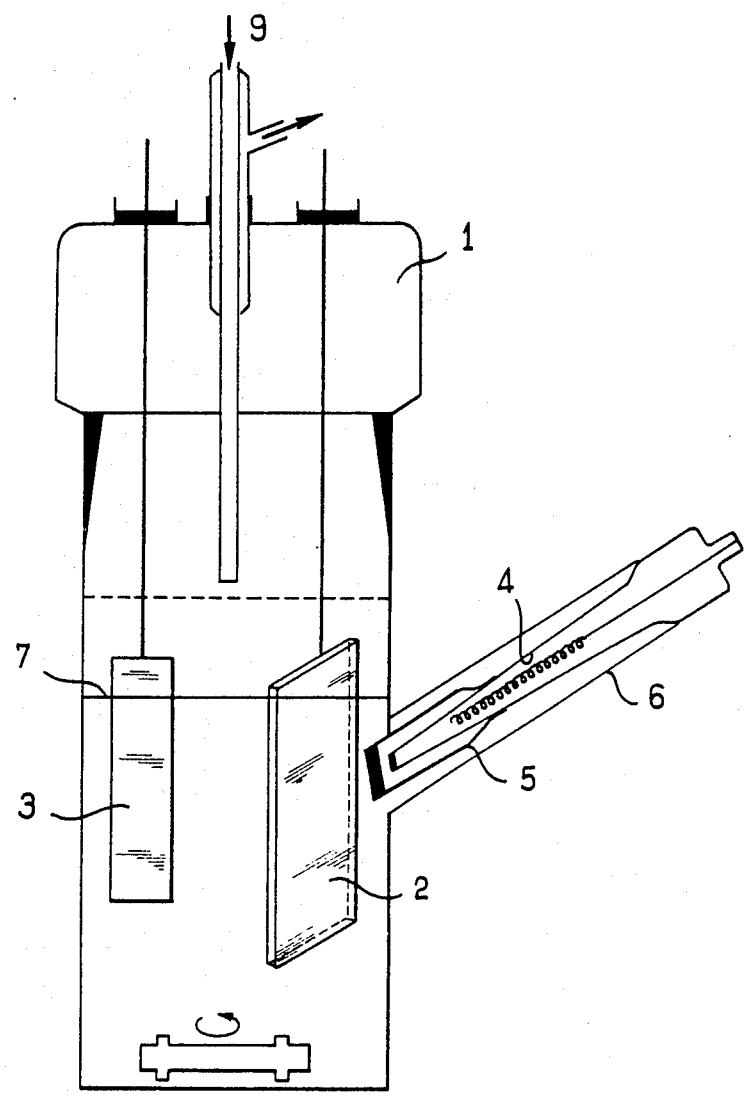
FIG. 1 is a diagrammatic side view of a cell used for performing the method.

FIG. 1 is a diagram of a cell suitable for use in the manufacturing method. This one-compartment cell 1 comprises a solid cathode 2 made in the form of a glass plate covered in ITO conductive oxide, a soluble anode 3 which is made of lithium, and a sloping extension 6 for a reference electrode 4 which is connected via a separating extender 5.

All three electrodes are immersed in an electrolyte and the electrolyte level is marked at 7.

A magnetic bar 8 at the bottom of the cell can be used for homogenizing the medium.

The top of the cell has an opening 9 for passing argon. The cell is used in air. It is air-tight and it is ventilated with a flow of argon. Its useful volume is 100 ml.

The electrolyte comprises 70 ml of THF and 30 ml of HMPT. These two solvents are advantageously prepared as follows:

70 ml of THF are placed on naphthalenesodium and distilled at atmospheric pressure under a flow of argon; and 30 ml of HMPT are placed on AlLiH$_4$ and are distilled under a primary vacuum established by a vane pump.

The electrodes used are as follows:

the Ag/Ag+ reference electrode 4 is dipped in a solution of 0.1 mole/liter of AgClO$_4$ in THF, it is located in an extension filled with the electrolyte;

the lithium anode 3 is in the form of a metal bar which has been scraped with a scalpel in THF and transferred in air into the synthesis cell; and the cathode 2 consists of a 13 mm × 37 mm glass plate covered with a 12 × 10$^{-8}$ m thick layer of conductive oxide (ITO, 50Ω/□), and annealed at 500° C. The non-conducting face is placed facing the lithium anode.

The following reagents are used:

the monomer is recrystallized dibromobiphenyl prepared by bromating biphenyl (1 mMole);

the catalyst is NiCl$_2$L$_2$ (0.25 mMole, where L$_2$ =(C$_6$H$_5$)$_2$—P—CH$_2$—CH$_2$—P—(C$_6$H$_5$)$_2$; and the background salt is LiClO$_4$ vacuum dried at 160° C. (0.03 Mole).

In addition, 110 mg of $MgBr_2$ may also be used, after being dried together with the $LiClO_4$.

The background salt and the magnesium salt are initially dissolved in the THF (by magnetic bar stirring). The HMPT is added after the salts have dissolved. A portion of this electrolyte is then poured into the reference extension.

The monomer and the catalyst are inserted into the cell

Polymerization takes place potentiostatically at $-2.5$ volts relative to the reference electrode. The average current observed is about 0.5 mA. Synthesis is stopped after a charge of 2 coulombs has passed.

The glass plate covered in conductive oxide is then removed from the synthesis cell and is washed in a THF bath.

After being blow-dried, it can be seen to covered with a semitransparent uniform film of neutral and insulating (nondoped) polyparaphenylene. This film is quite stable in air, and is thin and of uniform thickness (up to a thickness of about 1 $\mu$m). The polyparaphenylene is identified as such by:

infrared absorption giving bands at 999 $cm^{-1}$, 1483 $cm^{-1}$, 805 $cm^{-1}$ (bands which are associated with disubstituted phenyls), and at 767 $cm^{-1}$ and 694 $cm^{-1}$ (relatively weak bands which are associated with end-of-chain phenyls);

UV absorption giving a wide band with an absorption maximum around 370 nm; and

X-ray diffraction giving lines characteristic of PPP reflections (110), (200), (210) and (002).

The resulting PPP film is a semiconductor whose conductivity is low and less than $10^{-16} \Omega^{-1} cm^{-1}$. It is used in this non-doped form for making photovoltaic cells (example 1) and oxygen detectors/meters (example 2).

However, in order to make electrochromic cells (example 3) and batteries (example 4), the PPP film must be conductive.

The film is made conductive in accordance with the present invention by performing doping directly on the working electrode used in the manufacturing method.

Thus, starting with a PPP film prepared in accordance with the preferred implementation of the invention as described above, P-type electrochemical doping may be performed as follows:

the operations preferably take place in a glove box under an atmosphere of argon "c" and in the absence of water and oxygen;

the doping cell is preferably the bottom of a test tube containing about 10 ml; and the solvent is preferably propylene carbonate which has been twice distilled under vacuum in a teflon rotating band column maintained on a $4 \times 10^{-10}$ m molecular sieve.

A background salt such as $LiClO_4$ or $LiBF_4$ dried for several hours at 150° C. under vacuum is used at a concentration of 1 mole/liter. The electrodes are preferably as follows:

the counter-electrode which also serves as the reference electrode is a 0.38 mm $\times$ 5 mm $\times$ 10 mm strip of lithium (Alfa Products); and the working electrode is a glass electrode covered with ITO and PPP as mentioned above.

Once the salt has dissolved and both electrodes are installed, the PPP is maintained at a potential of 3.5V relative to the $Li/Li^+$ couple.

If voltage/current charts are made at regular intervals between 13.5V and 4.5V, a curve I(V) is obtained showing the current (in milliamps) as a function of the potential difference or "pd" (in volts) applied between said electrodes. The resulting curve is of the type shown in FIG. 2 where the current is low but increases over time.

After 100 hours, the chart is as shown in FIG. 2 (for an active area of about 1 $cm^2$). The growth of this phenomenon is explained by the need to wait for the electrolyte to diffuse into the film. Since the film is initially insulating, the electrochemical reaction must been at the ITO-PPP interface, so electrolyte must also be present at the interface.

The oxidation reaction which becomes significant at more than 4.1 volts is not complete at 4.5 volts. It is conventionally explained by partial oxidation of the polymer chains according to the following formula:

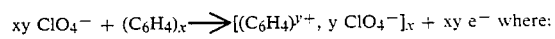

$$xy\ ClO_4^- + (C_6H_4)_x \longrightarrow [(C_6H_4)^{y+}, y\ ClO_4^-]_x + xy\ e^- \text{ where:}$$

x is the degree of polymerization; and y is the doping fraction.

The polymer is electrochromic. It absorbs light when in the oxidized state.

The absorption maximum of the oxidized polymer as observed using a sealed cell placed in a visible spectrometer lies at about 0.5 $\mu$m.

If the cell is excited with square-wave signals between 3.5V and 4.5V, an optical response is observed whose typical switching time is less than 100 milliseconds.

EXAMPLE 1

APPLICATION OF THE PPP FILM TO MAKING PHOTOVOLTAIC CELLS

FIG. 3 shows the current against potential difference characteristics of a photovoltaic cell which is being used to provide electric power. The current I is plotted in amps as a function of the potential difference pd in volts and the cell is an Al/PPP(1 $\mu$m)/ITO cell.

A conductive metal/PPP/electrode sandwich in which the PPP is prepared by the method of the present invention is observed in the presence of oxygen and under UV illumination to have the characteristics of a photovoltaic cell. A portion of the absorbed protons create charge carriers which, being separated by the electric field extending in a charge zone of the internal space of the polymer, are capable of providing energy to an external electric circuit.

A 1 $\mu$m thick PPP film (as measured using a scanning electron microscope) is deposited on a plate of ITO-covered glass as shown in FIG. 1.

Aluminum is evaporated onto to the PPP (to a thickness of $2 \times 10^{-7}$ m) through a mask which defines disks having a diameter of 1 mm.

Tests are then performed on a component constituted by a single 1 mm diameter disk of Al/PPP/ITO on which two contacts are made (a "+" contact being made by silver lacquer to the ITO, and a "−" contact by contact pressure against the aluminum).

This component is then illuminated through the ITO by monochromatic light centered on 429 nm (nanometers), at a power of 1 $\mu$W (microwatts).

The I(dp) characteristic which results from the illumination is shown in FIG. 3.

It can be seen that this component behaves like a photovoltaic cell capable of providing electric power: when under monochromatic illumination (0.43 μm) at 0.127 mw/cm$^2$:

the open circuit voltage is 1.3 volts;
the short circuit current is $2.1 \times 10^{-8}$ A/cm$^2$;
the efficiency is $5 \times 10^{-5}$; and
the scanning rate is 1 mV/sec.

Its behavior as a function of the incident wavelength shows a maximum response around 426.5 nm with the photocurrent falling off sharply when moving away from said value.

Photovoltaic cells which are transparent in the visible region of the spectrum can be made in this manner.

EXAMPLE 2
APPLICATION OF THE PPP FILM TO MAKING AN OXYGEN DETECTOR/METER

The electrical characteristics of the photovoltaic cells described in Example 1 change substantially as a function of the partial pressure of oxygen in the surrounding medium. The electrical characteristics of the cell thus constitute a probe responsive to the partial pressure of oxygen in the medium.

The photovoltaic cell described in Example 1 is used for this application.

The potential across its terminals is held to zero volts and the short-circuit current (Icc) under illumination at 0.43 μm is measured. A flow of nitrogen is passed over the component and a variable quantity of oxygen is mixed therewith (as measured out by a ball flow meter). The short-circuit current is observed to vary reversibly as a function of the oxygen partial pressure in the mixture (PPM).

| O$_2$ volume ppm | Icc $\times$ 10$^{-11}$ A |
| --- | --- |
| 100 000 | 4.2 |
| 30 000 | 3.6 |
| 10 000 | 3.2 |
| 5 000 | 2.8 |

It is thus shown that a thin layer of polyparaphenylene can be used for measuring oxygen partial pressures.

This effect may also be encountered with other oxidizing gases.

EXAMPLE 3
APPLICATION OF A DOPED PPP FILM TO MAKING ELECTROCHROMIC CELLS

A thin film of neutral PPP is transparent in the visible region of the spectrum, whereas such a film which has been P or N doped absorbs light in this region.

Since electrochemical P or N doping of PPP is reversible in some organic solvents, PPP must be considered as being an electrochromic substance in such media: it is transparent as a potential of 3 volts relative to the Li/Li$^+$ couple, and becomes optically absorbent above 4 volts (reddish color) and below 1 volt relative to the same reference. It typically passes from one state to another in 100 milliseconds.

This electrochromic behavior is observed during P-type electrochemical doping of the PPP film obtained by the method in accordance with the invention. This doping takes place as described above. Thus, the electrode which is quasi-transparent (slightly yellow) at 3.5 volts when the polymer is un-doped becomes dark red at a potential of 4.5 volts which corresponds to the chains being partially oxidized. Reversible electrochemical operation of this cell has been demonstrated.

This change in color can still be observed in a cell which has been cycled 30,000 times (where 1 cycle = 1 second at 3.5 volts and 1 second at 4.5 volts).

EXAMPLE 4
APPLICATION OF DOPED PPP TO IMPLEMENTING A BATTERY

The above described electrochromic cells may be used as secondary batteries, since P or N type electrochemical doping occurs in conjunction with reversible storage of positive or negative charges. Since the active electrode is a thin film, the capacity of such batteries is very low, however they are capable of being integrated in memory components, flat screens, etc. Thus, when making a battery having a thin film active electrode, the cell is the same as that used for doping. FIG. 2 shows that charge can be reversibly stored in and recovered from the polymer electrode.

When scanning at 100 mV/sec., which corresponds to a charge-discharge cycle taking place over 20 seconds, the quantity of charge involved is $0.8 \times 10^{-3}$ coulomb/cm$^2$, with the voltage dropping on discharge from 4.5 to 3.5 volts relative to the Li/Li$^+$ couple.

If the scanning speed is reduced to 20 mV/sec, the quantity of stored charge rises to $1.7 \times 10^{-3}$ coulomb/cm$^2$. The possibility of using a thin film of PPP deposited on ITO as the active electrode of a secondary battery has thus been demonstrated. The fact that new technologies are based on ITO being deposited on glass (for example in flat screens), opens the perspective of batteries being integrated in this type of component.

We claim:

1. A method of manufacturing a polyparaphenylene film by electro-polymerization, comprising the step of:
    electrochemically reducing a monomer of the formula

wherein n is an integer ranging from 1 to 4, in a one-compartment electrochemical cell which comprises a reference electrode, a working electrode comprising a solid cathode, and a counter electrode, said electrodes being immersed in an electrolyte which includes one or more aprotic solvents, with at least one of said solvents being bipolar, an anhydrous background salt and an organometallic catalyst of the formula:

NiX$_2$L wherein X is a halogen and L is a binder, and wherein the ratio of said catalyst to said monomer is in the range from about 0.1 to 1.

2. A method according to claim 1, wherein said catalyst-to-monomer ratio is about 0.25.

3. A method according to claim 1, wherein said solid cathode comprises a material selected from the group consisting of graphite, vitreous carbon, gold, nickel, platinum, conductive SnO$_2$-covered glass, indium tin oxide-covered glass, and metal-covered glass.

4. A method according to claim 3, wherein said cathode is indium tin oxide-covered glass.

5. A method according to claim 1, comprising the further step of applying a voltage to said cathode in the range of about −2.2 to −2.8 volts relative to the reference electrode.

6. A method according to claim 1, wherein said reference electrode comprises silver/silver perchlorate.

7. A method according to claim 1, wherein said counter electrode is an anode of a material selected from the group consisting of soluble lithium, soluble magnesium, non-soluble gold and non-soluble platinum.

8. A method according to claim 1, wherein said electrolyte comprises a mixture of $\frac{2}{3}$ by volume aprotic solvent and $\frac{1}{3}$ by volume bipolar solvent.

9. A method according to claim 8, wherein said electrolyte comprises a mixture of $\frac{2}{3}$ THF by volume and $\frac{1}{3}$ HMPT by volume.

10. A method according to claim 1, wherein said background salt is selected from the group consisting of $LiClO_4$, $NaBF_4$ and $NBu_4BF_4$.

11. A method according to claim 1, wherein n is an integer from 1 to 2.

* * * * *

UNITED STATES PATENT OFFICE
CERTIFICATE OF CORRECTION

Patent No. 4,863,574            Dated September 5, 1989

Inventor(s) Francois Maurice, Gerard Froyer, Yvan Pelous, Michel Petit, Jean-Francois Fauvarque It is certified that error appears in the above-identified patent and that said Letters Patent is hereby corrected as shown below:

Column 6, Line 2, change "13.5V" to --3.5V--

Signed and Sealed this

Twenty-eighth Day of August, 1990

Attest:

HARRY F. MANBECK, JR.

Attesting Officer    Commissioner of Patents and Trademarks

UNITED STATES PATENT OFFICE
CERTIFICATE OF CORRECTION

Patent No. 4,863,574  Dated September 5, 1989

Inventor(s) Francois Maurice, Gerard Froyer, Yvan Pelous, Michel Petit, Jean-Francois Fauvarque It is certified that error appears in the above-identified patent and that said Letters Patent is hereby corrected as shown below:

ON THE TITLE PAGE

Change Assignee: "Centre National de la Recherche Scientifique, Paris, France"

to -- ETAT FRANCAIS, représenté par le Ministre des PTT (Centre National d'Etudes des Télécommunications) CENTRE NATIONAL DE LA RECHERCHE SCIENTIFIQUE (CRNS)

Signed and Sealed this

Twelfth Day of October, 1993

Attest:

BRUCE LEHMAN

*Attesting Officer*    *Commissioner of Patents and Trademarks*